United States Patent [19]

Segers

[11] Patent Number: Plant 6,600

[45] Date of Patent: Feb. 14, 1989

[54] CARNATION VARIETY NAMED BAGATEL

[75] Inventor: Theo Segers, Hoofddorp, Netherlands

[73] Assignee: Euser's Greenhouses, Inc., Wheat Ridge, Colo.

[21] Appl. No.: 94,123

[22] Filed: Sep. 8, 1987

[51] Int. Cl.[4] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new spray carnation particularly distinguished by its pure white blooms of medium size which are produced profusely and continuously the year around on relatively short peduncles vertically spaced at the top end of a flowering stem having an average height of between 150 and 160 cm. This plant branches readily and has a sturdy, upright growth habit with good strength and abundant foliage.

1 Drawing Sheet

BACKGROUND OF THE NEW PLANT

This new carnation cultivar originated as a seedling resulting from my crossing of selected varieties from my collection of carnation plants maintained for breeding purposes in my greenhouses at Hoofddorp, The Netherlands, with the object of producing new spray carnations with good resistance to *Fusarium oxysporum* and *Fusarium redolens.* This particular seedling was selected for propagation because of the pure white coloration of its medium sized flowers, which were produced on long, strong stems, and propagation of this selected variety was done by me at Hoofddorp by means of cuttings with very satisfactory results; and continued propagation of this variety at Hoofddorp through several successive generations, by means of cuttings, has demonstrated that the novel characteristics of this plant would hold true from generation to generation and appeared to be firmly fixed.

DESCRIPTION OF THE DRAWING

My new spray carnation is illustrated by the accompanying photographic drawing, which shows the inflorescence on a stem of a fully grown plant, the view including buds and flowers in several stages of development, together with fully opened blossoms, and showing buds in several stages of opening.

DESCRIPTION OF THE NEW PLANT

The following is a detailed description of my new spray carnation cultivar based upon observations of plants grown under conventional greenhouse procedures at Hoofddorp, The Netherlands, the color designations being according to The R.H.S. Colour Chart published by The Royal Horticultural Society of London, England.

THE PLANT

Origin: Seedling.

Parentage:

*Seed parent.*—Stock Variety IVT 72.005.3, unnamed and unpatented and identified in my breeding records.

*Pollen parent.*—'Lilli-Ann' (unpatented).

Classification:

*Botanic.*—*Dianthus caryophyllus.*

*Commercial.*—Spray Carnation.

Form: Tall, upright bush.

Height: About 150 to 160 cm.

Growth rate: Moderate, flowering in about six months following the first planting.

Branching: Good; about 5 to 6 breaks.

Stem size: About 4 to 6 mm.

Foliage:

*Quantity.*—Abundant.

*Number of leaves.*—Too numerous to count.

*Leaf size.*—About 125 mm. long with entire margins.

*Leaf shape.*—Sessile.

*Texture.*—Leathery.

*Color.*—Upper side — Olive Green. Under side — Blue Green.

THE BUD

Form: Inverted pear-shaped.

Size: Medium. Diameter — About 15 mm. Depth — About 25 mm.

Opening rate:

*Bud to flower.*—About 10 days.

Color: When sepals first divide and when petals begin to unfurl, Light green.

Character: The sepals are connected together at the calyx and extend upwardly with a generally ovate form and acute apex. The sepals curl back slightly when the flower opens.

Calyx:

*Shape.*—Pear-shaped.

*Size.*—Medium; about 10 mm. wide and about 8 mm. long.

*Aspect.*—Smooth.

*Splitting.*—The calyx splits slightly for about 10 mm. from the top.

Peduncle:

*Length.*—About 5 mm.

*Color.*—Blue Green.

*Character.*—Erect and rigid.

THE FLOWER

Blooming habit: Continuous and profusely the year around.

Size of bloom: Medium.

*Diameter.*—About 40 mm.

*Depth.*—About 7 mm.

Borne: Singly on strong, upright pedicels, with 4 to 6 flowers spaced vertically at the top of a main stem.
Shape: High centered when the bloom first opens and as the bloom matures.
Petalage:
*Number of petals.*—About 29.
*Arrangement.*—Imbricated.
*Shape of petals.*—Fan-shaped with slightly serrate margins.
*Texture.*—Soft.
*Aspect.*—Velvety.
*Color.*—Outer petals: Body — White. Base — Light Green. Inside petals: Body — White. Base — Light Green. Reverse side — White.
Petaloids:
*Number.*—About 28.
*Size.*—About 35 mm. long and about 15 mm. wide.
*Color.*—White.
Peduncle:
*Length.*—About 5 mm.
*Color.*—Blue Green.
*Character.*—Upright and sturdy.
Persistence: The petals hang on and dry.
Fragrance: Light.
Lasting quality:

*On the plant.*—About 5 to 6 days after blooming.
*As a cut flower.*—About 10 days in vase keeping.

THE REPRODUCTIVE ORGANS

Stamens:
*Number.*—About 22.
*Arrangement.*—Clustered.
*Filaments.*—Length: About 15 to 28 mm. Color: Yellow White.
*Pollen.*—Color: Cream.
Pistils:
*Number.*—One.
*Style.*—Length: About 21 mm. Color: White.
*Stigma.*—Color: White.
Character of ovaries: Superior.
Color: Light Green.

I claim:

1. The new and distinct spray carnation cultivar and parts thereof, substantially as herein shown and described, particularly characterized by its profuse production of medium sized, pure white flowers spaced vertically adjacent the top of a tall flowering stem having abundant foliage and a strong, sturdy, upright growth habit.

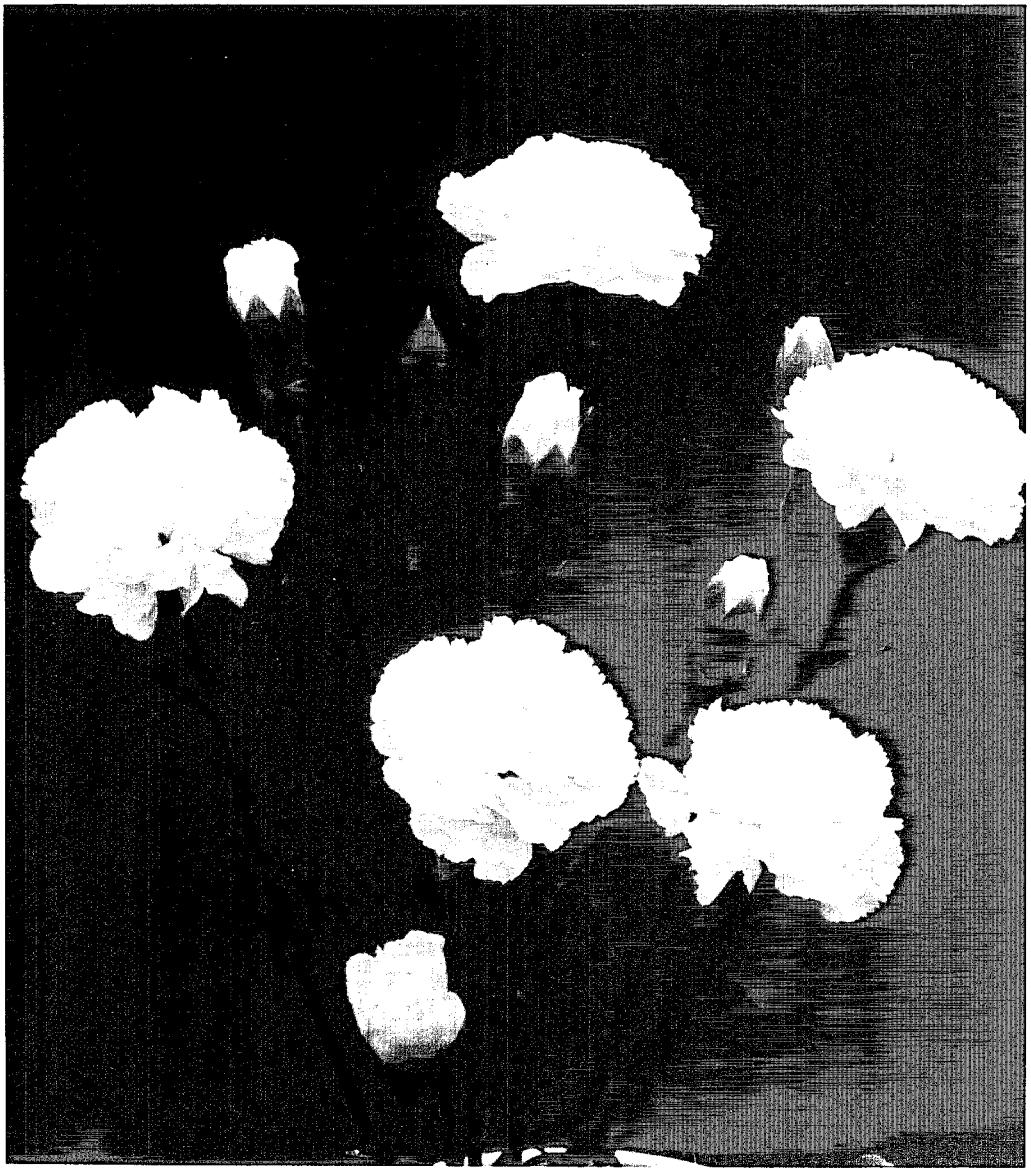

* * * * *